United States Patent
Huber

Patent Number: 6,018,044
Date of Patent: Jan. 25, 2000

[54] LIGHT SCREENING COMPOSITIONS

[75] Inventor: Ulrich Huber, Erlenbach, Switzerland

[73] Assignee: Roche Vitamins Inc., Parsippany, N.J.

[21] Appl. No.: 09/219,943

[22] Filed: Dec. 23, 1998

[30] Foreign Application Priority Data

Jan. 2, 1998 [EP] European Pat. Off. ............. 98100008
Nov. 24, 1998 [EP] European Pat. Off. ............. 98122321

[51] Int. Cl.⁷ .................. C07D 251/24; C07D 251/70
[52] U.S. Cl. ............................................................ 544/197
[58] Field of Search ............................................. 544/197

[56] References Cited

U.S. PATENT DOCUMENTS

| | | | |
|---|---|---|---|
| 4,617,390 | 10/1986 | Hoppe et al. | 544/197 |
| 5,053,290 | 10/1991 | Canivenc | 528/26 |
| 5,185,445 | 2/1993 | Meuwly et al. | 544/216 |
| 5,233,040 | 8/1993 | Raspanti | 544/197 |
| 5,786,475 | 7/1998 | Fuso et al. | 544/212 |

FOREIGN PATENT DOCUMENTS

| | | |
|---|---|---|
| 358 584 | 3/1990 | European Pat. Off. . |
| 358584 | 3/1990 | European Pat. Off. . |
| 538 431 | 4/1993 | European Pat. Off. . |
| 693 483 | 1/1996 | European Pat. Off. . |
| 704 437 | 4/1996 | European Pat. Off. . |
| 704 444 | 4/1996 | European Pat. Off. . |
| 780 382 | 6/1997 | European Pat. Off. . |

*Primary Examiner*—John M. Ford
*Assistant Examiner*—V Balasubramanian
*Attorney, Agent, or Firm*—Mark E. Waddel; Stephen M. Haracz; Bryan Cave LLP

[57] ABSTRACT

The present invention concerns new s-triazines of the formula

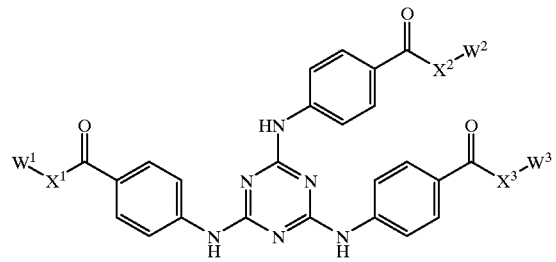

wherein
$W^1$, $W^2$ and $W^3$ each independently signifies $C_1$–$C_{20}$ alkyl or a group SpSil;
$X^1$, $X^2$ and $X^3$ each independently signifies O or NH;
Sp signifies a spacer group;
Sil signifies a silane, an oligosiloxane or a polysiloxane moiety; with the proviso that at least one of $W^1$, $W^2$ and $W^3$ signifies SpSil.

27 Claims, No Drawings

LIGHT SCREENING COMPOSITIONS

FIELD OF THE INVENTION

The present invention relates to new s-triazines, a process for their manufacture and the use thereof as UV-B filters in light screening compositions, especially for the preparation of a cosmetic composition useful for protecting human skin from sunlight radiation.

BACKGROUND OF THE INVENTION

Many sunscreen agents have been described and developed in the past proposing 1,3,5 triazines as UV-B stabilizers. An example for such a triazine-compound is 4,4',4"-(1,3,5-triazine-2,4,6-triyltriimino)-tris-benzoic acid-tris(2-ethylhexyl ester) sold under trade name UVINUL T-150.

In the German Patent Publication DE-OS 3 206 3987 which is an equivalent of U.S. Pat. No. 4,617,390, s-triazine derivatives are disclosed which highly absorb in the UV-B region and are obtained by reacting trichloro-triazine with p-aminobenzoic acid esters. However, these compounds are very poorly soluble in the solvents commonly used in the formulations of sunscreen agents, thus limiting their use as ingredient of emulsions and cosmetic formulations, particularly when an increased dosage of the sunscreen agent is needed. In addition those filters tend to crystallise on the skin leaving a sandy skin feeling and reducing the sun protection factor (SPF) essentially.

SUMMARY OF THE INVENTION

The present invention provides s-triazine compounds that absorb in the UV-B region and show a good solubility in solvents commonly used in sunscreen agents. Light screening compositions which include one or more of the present compounds and which are suitable as cosmetic formulations are provided.

Also provided are methods of preparing the compounds in accordance with the present invention.

DETAILED DESCRIPTION OF THE INVENTION

It has now been found that compounds of the general formula I below besides absorbing in the UV-B region show a good solubility in solvents commonly used in sunscreen agents. Compounds of formula I can be used in preparing a light screening composition, such as a cosmetic composition, useful for protecting human skin from sunlight radiation.

Compounds of the general formula I are as follows:

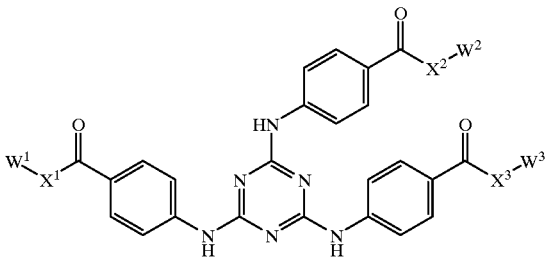

I wherein
$W^1$, $W^2$ and $W^3$ each independently signifies $C_1$–$C_{20}$ alkyl or a group Sp—Sil;
$X^1$, $X^2$ and $X^3$ each independently signifies O or NH;
Sp signifies a spacer group;
Sil signifies a silane, an oligosiloxane or a polysiloxane moiety; with the proviso that at least one of $W^1$, $W^2$ and $W^3$ signifies SpSil.

Preferably $W^1$, $W^2$ and $W^3$ signify SpSil; or $W^1$ and $W^2$ signify $C_1$–$C_{20}$ alkyl, preferably $C_6$–$C_{10}$-alkyl, most preferably 2-ethylhexyl, and $W^3$ signifies SpSil.

Preferably $X^1$, $X^2$ and $X^3$ signify oxygen, or $X^1$ and $X^2$ signify oxygen and $X^3$ signifies NH.

The term "spacer group" refers in this context to a $C_3$–$C_{12}$ divalent alkyl or alkylene chain which links the silane, oligosiloxane or polysiloxane moiety to the triazine residue. In said chains one or several carbon atoms may be replaced by oxygen atoms resulting in groups such as —$C_1$–$C_6$-alkyl-O—$C_1$–$C_5$-alkyl- e.g. —(CH$_2$)$_2$—O—(CH$_2$)$_2$— or —(CH$_2$)$_4$—O—(CH$_2$)$_2$—; —$C_1$–$C_6$-alkenyl-O—$C_1$–$C_5$-alkyl- e.g. —C(=CH$_2$)—(CH$_2$)$_2$—O—(CH$_2$)$_4$—; —$C_1$–$C_4$-alkyl-O—$C_1$–$C_4$-alkyl —O—$C_1$–$C_2$-alkyl e.g —(CH$_2$)$_2$—O—(CH$_2$)$_2$—O—(CH$_2$)$_2$— and the like.

The term "$C_3$–$C_{12}$ divalent alkyl chain" embraces straight chain or branched saturated hydrocarbon residues such as 3-propylene, 2-propylene, 2-methyl-3-propylene, 3-butylene, 4-butylene, 4-pentylene, 5-pentylene, 6-hexylene, 12-dodecylene and the like.

The term "$C_3$–$C_{12}$ divalent alkylene chain" embraces straight chain or branched unsaturated hydrocarbon residues containing one or multiple double bonds such as 2-propen-2-ylene, 2-propen-3-ylene, 2-methyl-3-propenylene, 3-buten-3-ylene 3-buten-4-ylene, 4-penten-4-ylene, 4-penten-5-ylene, (3-methyl)penta-2,4-dien-4 or 5-ylene, 11-dodecen-11-ylene and the like.

Preferred spacer groups are: .—(CH$_2$)$_3$—, —(CH$_2$)$_4$—, —(CH$_2$)$_5$—, —(CH)(CH$_3$)—(CH$_2$)—, —(CH$_2$)$_2$—CH=CH—, —C(=CH$_2$)—CH$_2$—, —C(=CH$_2$)—(CH$_2$)$_2$—O—(CH$_2$)$_4$—, (CH$_2$)$_4$—O—(CH$_2$)$_2$—.

The term "silane" refers in this context to a group SiR$^1$R$^2$R$^3$ wherein R$^1$, R$^2$ and R$^3$ each independently signify $C_1$–$C_6$ alkyl, $C_1$–$C_6$ alkoxy or phenyl.

The term "alkyl" and "alkoxy" residues can be straight-chain or branched residues with the number of carbon atoms indicated such as e.g. methyl, ethyl, propyl, isopropyl, n-butyl, tert.butyl, 2-ethylhexyl, thexyl, (1,1,2-trimethylpropyl) and, respectively, methoxy, ethoxy, propoxy, isopropoxy, n-butoxy, tert.butoxy, 2-ethylhexoxy, thexoxy.

Examples for the group $SiR^1R^2R^3$ are: $Si(CH_3CH_3)_3$, $Si(CH_2-CH_3CH_3)_3$, $Si(isopropyl)_3$, $Si(tert.butyl)_3$, $SiMe_2tert.butyl$, $SiMe_2thexyl$, $Si(OMe)_3$, $Si(OEt)_3$, $SiPh_3$ and the like, preferably $Si(CH_2-CH_3)_3$- and $Si(CH_2-CH_2-CH_3)_3$.

The term "oligosiloxane" refers in this context to groups of the general formula $SiR^{10}{}_m(OSiR^{10}{}_3)_n$ with m=0, 1 or 2; n=3, 2 or 1 and m+n=3; or groups of the general formula IIa, IIa' or IIb

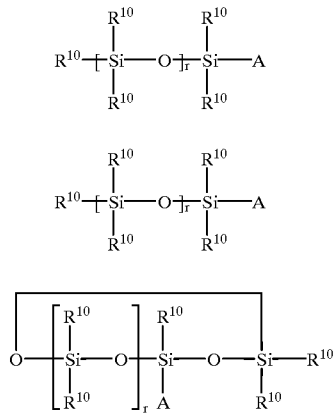

wherein

A signifies a bond to the spacer;
$R^{10}$ signifies $C_1$–$C_6$ alkyl or phenyl;
r signifies 1 to 9, preferably 1 to 3.

The term "polysiloxane" refers in this context to groups of the general

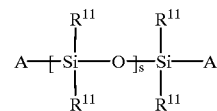

formula IIIa or IIIb,

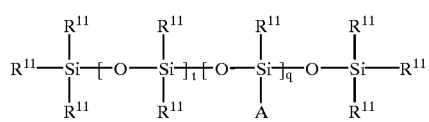

wherein

A is a bond to the spacer;
$R^{11}$ signifies $C_1$–$C_6$ alkyl or phenyl;
s has a value of from 4 to 250, preferably 5 to 150;
t has a value of from 5 to 250, preferably 5 to 150, more preferably a statistical mean of about 60;
q has a value of from 1 to 30, preferably 2 to 10, more preferably a statistical mean of about 4.

The residues $R^{10}$ and $R^{11}$ are preferably $C_1$–$C_6$ alkyl, more preferably $C_1$–$C_4$ alkyl, most preferably methyl.

In one particular embodiment of the invention $W^1$, $W^2$ and $W^3$ signify Sp'—Sil'. Said embodiment refers to compounds of the formula Ia:

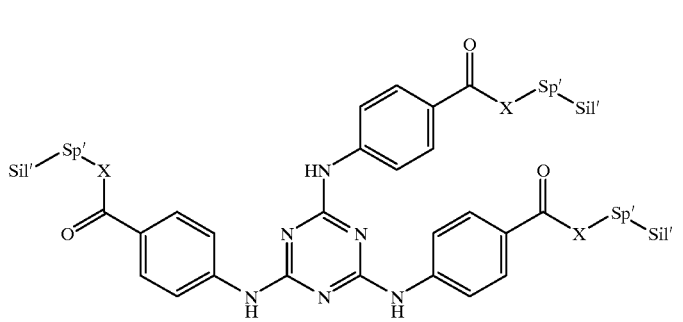

wherein

X signifies O or NH;
Sp' signifies a straight-chain or branched saturated or single or multiple unsaturated hydrocarbon group of 3 to 12 carbon atoms;
Sil' signifies the group $SiR^1R^2R^3$, wherein $R^1$, $R^2$ and $R^3$ each independently signify $C_1$–$C_6$-alkyl, $C_1$–$C_6$-alkoxy or phenyl; or an oligosiloxane of the formula —$SiMe_m$ $(OSiMe_3)_n$, wherein Me is methyl and m is 0, 1 or 2, n is 1, 2 or 3 and m+n are 3; or an oligosiloxane of the formulae A, A' and B

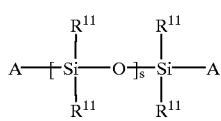

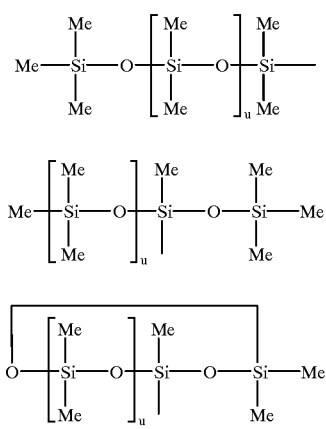

wherein Me is methyl and u is 0 to 6.

Especially preferred compounds of formula I are:

2,4,6-Tri-anilino-p-{carbo-4'-(1,1,3,3,3-pentamethyldisiloxanyl)-1'-butyloxy}-1,3,5-triazine, 2,4,6-Tri-anilino-p-{carbo-4'-(1,1,1,3,5,5,5-heptamethyl trisiloxanyl)-1'-butyl-oxy}-1,3,5-triazine, 2,4,6-Tri-anilino-p-{carbo-2'-methyl-3'-(1,1,3,3,3-pentamethyl disiloxanyl)-1'-propyloxy}-1,3,5-triazine, 2,4,6-Tri-anilino-p-{carbo-5'-(1,1,3,3,3-pentamethyl disiloxanyl)-1'-pentyloxy}-1,3,5-triazine, 2,4,6-Tri-anilino-p-{carbo-3'-(1,1,3,3,3-pentamethyl disiloxanyl)-1'-propyloxy}-1,3,5-triazine, 2,4,6-Tri-anilino-p-{carbo-4'-(triethyl silyl)-1'-butyloxy}-1,3,5-triazine, 2,4,6-Tri-anilino-p-{carbo-4'-(triethly silyl)-1'-but-3-enyloxy}-1,3,5-triazine, 2,4,6-Tri-anilino-p-{carbo-7'-(triethyl silyl)-4'-oxa-heptyloxy}-1,3,5-triazine, 2,4-Di-anilino-p-carbo-(2'-ethyl-hexyloxy)-6-anilino-p-{carbo-7'-(1,1,3,3,3-pentamethyl disiloxanyl )-4'-oxa-heptyloxy}-1,3,5-triazine, 2,4-Di-anilino-p-carbo-(2'-ethyl-hexyloxy)-6-anilino-p-{carbo-7'-(1,1,1,3,5,5,5-heptamethyl trisiloxanyl)-4'-oxa-heptyloxy}-1,3,5-triazine, 2,4-Di-anilino-p-carbo-(2'-ethyl-hexyloxy)-6-amino{N-(-2'-(1,1,1,3,5,5,5-heptamethyl trisiloxanyl)-allyl)-p-benzamidyl}-1,3,5-triazine, and a triazine as disclosed in Example 15.

The compounds according to the present invention absorb UV radiations in the range from 290 to 320 nm and show an improved solubility in lipophilic solvents. Furthermore, they can easily be dispersed in emulsions and have relatively low tendency to crystallise in emulsions or on the skin. Thus, the compounds of the present invention can be used for the preparation of light screening compositions, especially for the preparation of a cosmetic composition useful for protecting human skin from sunlight radiation. These products can be applied in high concentrations which effect improved sun protection. Effects of aggregation and crystallisation which furnish a loss in efficacy are reduced in the emulsions and on the skin.

The present invention also provides light screening compositions containing one or more compounds of formula I as sunscreen agents.

The present invention further provides a process for the preparation of the compounds of formula I.

The synthesis of the compounds of formula I, wherein $W^1$, $W^2$ and $W^3$ signify SpSil can be carried out according to the following steps I to III:

Step I

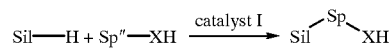

wherein Sil and X are as defined above; Sp" has the same meaning as Sp defined above, except that it has one degree of unsaturation more than Sp. In other words, if Sp" has one double bond Sp is saturated and if Sp" has a triple bond or two double bonds Sp has one double bond.

Step II

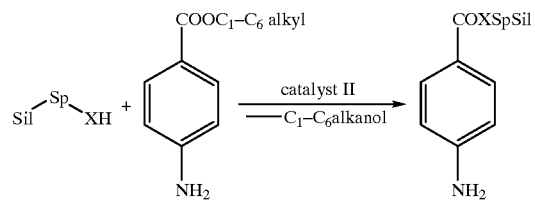

wherein Sil, Sp and X are as defined above.

Step III

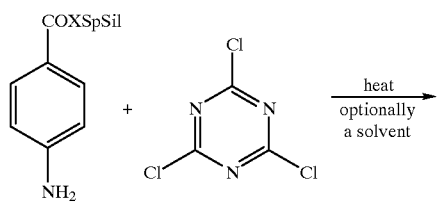

-continued

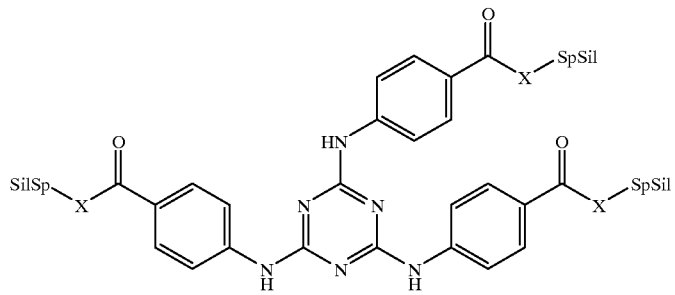

wherein Sil, Sp and X are as defined above.

The first step is a hydrosilylation reaction and can be performed according to methods known per se, such as at a temperature in the range of 0° to 200° C., preferably 40° to 110° C. in the presence of a metal catalyst. The reaction is preferably carried out in an inert gas atmosphere, optionally in a solvent. Suitable catalysts are platin catalysts like metallic Pt on carbon, chloroplatinic acid, divinyl-tetramethyl-disiloxane platinum complex, or any other platinum complex; rhodium catalysts like metallic Rh 5% on carbon, bis(1,5-cyclooctadien)-di-Rh(I)-dichloride and the like; Mo, Ru, Pd, Cr, Fe, Co, Ni or Cu in their metallic form or as a complex. The catalysts can be homogeneous or heterogeneous. Most organic solvents can be used such as aromatic solvents, preferably toluene, xylene, pyridine; ether such as THF, dioxane and the like, aliphatic solvents such as dichloroethane, dichloromethane, chloroform, $CCl_4$, acetonitrile, DMF, DMSO, ethanol and the like.

The second step is a transesterification or an amide formation and can be performed according to methods known per se using a catalyst II. Thus, the reaction can be carried out at a temperature in the range of 50° to 250° C., optionally in a solvent. Organic solvents as listed under the first step can be used. Suitable catalysts are basic catalysts such as KOH, $Na_2CO_3$ and the like, acidic catalysts such as $H_2SO_4$, HCl and the like or a Lewis acid catalyst like e.g. tetraisopropyl orthotitanate.

The third step can be achieved just by treating slowly the product of the second step and cyanuric acid chloride at a temperature in the range of 20° to 280° C., preferably of 50° to 150° C. without or with an appropriate solvent (e.g. toluene, xylene). Optionally a base can be present such as $K_2CO_3$, NaH and the like.

The sequence of steps can be freely interchanged, e.g. it is possible to start with step III by treating cyanuric acid chloride with $C_{1-6}$-alkyl 4-aminobenzoic acid ester followed by a transesterification or an amide formation (step II) and finishing with the hydrosilylation step I.

The synthesis of the compounds of formula I, wherein one or two groups W signify $C_1$–$C_{20}$ alkyl and the remaining group W signifies SpSil can also be carried out comparable to the above reaction scheme. Cyanuric acid chloride is treated either at first with 4-aminobenzoic acid $C_1$–$C_{20}$ alkyl ester at a temperature in the range of 0° to 40° C., and then with a compound of the formula C

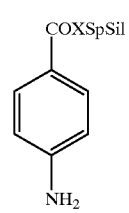

C wherein X, Sp and Sil are as defined above at a temperature in the range of 20° to 280° C., or cyanuric acid chloride is treated at first with a compound of the formula C at a temperature in the range of 0° to 40° C. and then with 4-aminobenzoic $C_1$–$C_{20}$ alkyl ester at a temperature in the range of 20° to 280° C.

Compounds of the formula I, wherein Sil is a polysiloxane are preferably prepared according to the following schema:

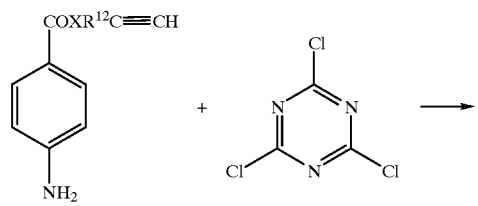

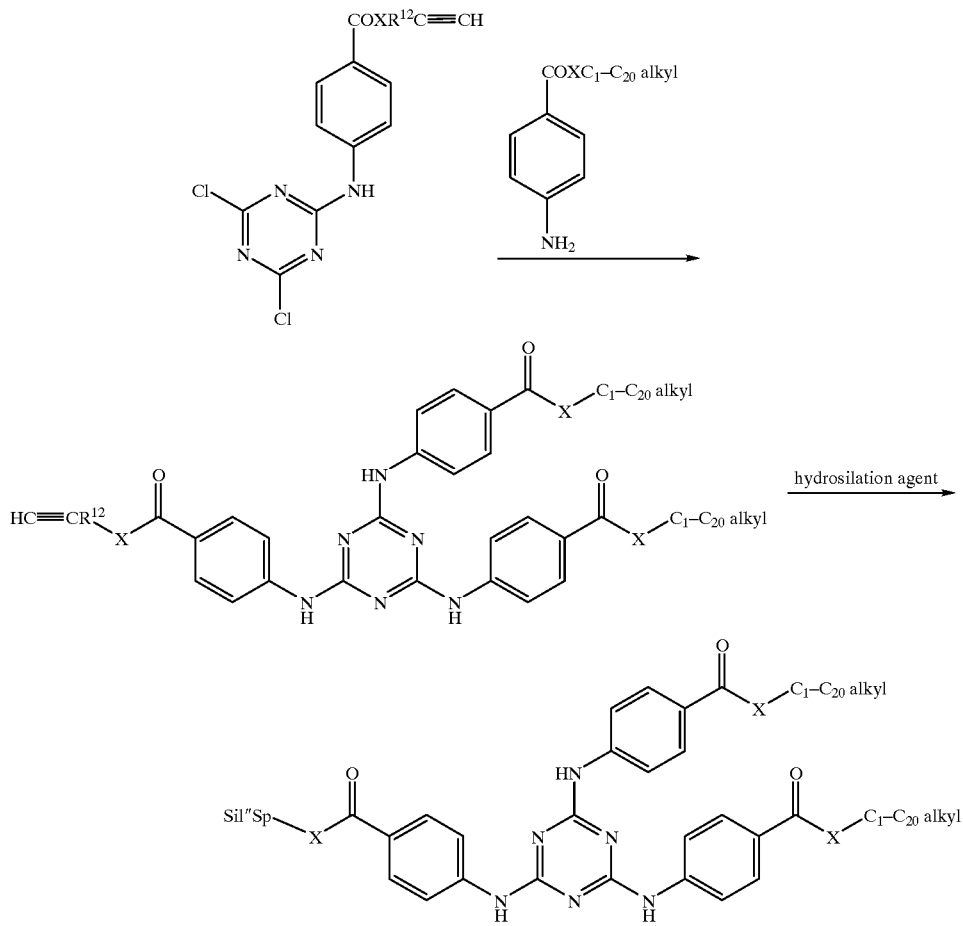

-continued wherein X and Sp are as defined above, Sil″ is a polysiloxane as defined above and $R^{12}$ is a $C_1$–$C_{10}$ divalent alkyl chain or a $C_3$–$C_{10}$ divalent alkyl chain optionally interrupted by at least one oxygen atom.

Compounds according to the invention are colourless or slightly yellowish liquids, semiliquids or crystalline compounds. They are especially qualified as light screening agents because of their high absorption of UV-B light, their good solubility in organic solvents, especially in solvents commonly used in cosmetic industry and because of their easy and cheap access. They can be combined with one or more known UV-B and/or UV-A filters.

The preparation of novel light screening agents, especially of preparations for skin protection and, respectively, sunscreen preparations for everyday cosmetics, comprises incorporating a compound of formula I in a cosmetic base which is usual for light screening agents. Where convenient, other conventional UV-A, and respectively, UV-B filters can also be combined during this incorporation. Said combinations of UV filters can show a synergistic effect. The preparation of said light screening agents is well known to the skilled artisan in this field. The amount of compounds of the general formula I and other known UV-filters is not critical. Suitable amounts are from 0.1 to 20%, preferably about 0.5 to about 12% by weight with respect to the composition.

Suitable UV B filters, i.e. substances having absorption maxima between about 290 and 320 nm, are for example the following organic compounds which belong to a large group of substances:

p-Aminobenzoic acid derivatives such as ethyl, propyl, butyl, isobutyl, octyldimethyl, amyldimethyl, ethoxylated ethyl, propoxylated ethylglyceryl or ethylglycosyl p-aminobenzoate and the like;

Acrylates such as 2-ethylhexyl 2-cyano-3,3-diphenylacrylate (octocrylene), ethyl 2-cyano-3,3-diphenylacrylate and the like;

Aniline derivatives such as methyl anilinum methosulfate and the like;

Anthranilic acid derivatives such as menthyl anthranilate and the like;

Benzophenone derivatives such as benzophenone-1 to benzophenone-12 and the like.

Camphor derivatives such as methyl benzylidene camphor, 3-benzylidene camphor, camphor benzalkonium methosulfate, polyacrylamidomethyl benzylidene camphor, sulfo benzylidene camphor, sulphomethylbenzylidene camphor, therephthalidene dicamphor sulfonic acid and the like;

Cinnamate derivatives such as octyl methoxycinnamate or ethoxyethyl methoxycinnamate, diethanolamine methoxycinnamate, isoamyl methoxycinnamate and the like as well as cinnamic acid derivatives bond to siloxanes;

Gallic acid such as digalloyl trioleate and the like;

Imidazole derivatives such as phenyl benzimidazole sulfonic acid and the like;

Salicylate derivatives such as isopropylbenzyl, benzyl, butyl, octyl, isooctyl or homomenthyl salicylate and the like;

Triazole derivatives such as drometriazole, hydroxydibutylphenyl-, hydroxydiamylphenyl-, hydroxyoctylphenyl- or hydroxyphenylbenztriazole and the like;

Triazone derivatives such as octyl triazone and the like; and

Pigments such as microparticulated $TiO_2$, ZnO and the like.

The formulation may further contain UV-A filters such as

Dibenzoylmethane derivatives such as 4-tert. butyl-4'-methoxydibenzoyl-methane and the like;

Triazine compounds as described in the European Patent Publications EP 0693483 A1, EP 0704437 A2, EP 0704444 A1 and EP 0780382 A1;

Organosiloxane compounds as described in the European Patent Publications EP 0538431 B1, EP 0709080 A1 and EP 0358584B1;

Malonates such as described in the European Patent Application 98114262.3

Especially useful for effective UV absorption are combinations with metallo-oxy nano pigments like e.g. titanoxide, zincoxide, ceroxide, zircon oxide, ferrous oxide and mixtures thereof, the diameter of which is <100 nm.

The following Examples 1–15 further illustrate the invention but do not limit its scope in any manner.

Examples 8 and 9 are comparative examples. Example 16 refers to a light screening composition.

EXAMPLE 1

Preparation of 2,4,6-tri-anilino-p-{carbo-4'-(1,1,3,3,3-pentamethyl-disiloxanyl)-1'-butyloxy}-1,3,5-triazine.

a) First step: preparation of 4-(1,1,3,3,3-pentamethyl disiloxanyl)-1-butanol.

A 50 ml reaction flask was charged with 10.3 ml 3-butene-1-ol and a catalytic amount of divinyl-tetramethyl disiloxane platinum complex under inert atmosphere and heated to 60° C. 19.5 ml of pentamethyl disiloxane was slowly added through a dropping funnel. The reaction mixture was stirred at 75 to 80° C. for three hours, followed by distillation at 110 to 115° C./38×10² Pa over a 10 cm column. Yield 18.9 g (86% of theoretical) of a clear liquid.

b) Second step: preparation of 4-aminobenzoic acid 4-(, 1,3,3,3-pentamethyl disiloxanyl) butyl ester.

A 50 ml reaction flask was charged with 9.9 g of ethyl 4-aminobenzoic acid ester, 15.3 g of 4-(1,1,3,3,3-pentamethyl disiloxanyl)-1-butanol and 0.06 ml of tetra-isopropyl orthotitanate and heated to 110° C./90×10² Pa for 7 h. The ethanol formed was subsequently distilled off. The product was fractionated at 205° C./0.06×10² Pa to yield 12.6 g (62% of theoretical) of a clear liquid.

c) Third step: preparation of 2,4,6-tri-anilino-p-{carbo-4'-(1,1,3,3,3-pentamethyl disiloxanyl)-1'-butyloxy}-1,3,5-triazine.

In a 400 ml reaction flask 10.2 g of 4-aminobenzoic acid 4-(1,1,3,3,3-pentamethyl disiloxanyl) butyl ester were dissolved in 150 ml of toluene and cooled to 0° C. A solution of 1.83 g of cyanuric acid chloride in 60 ml of toluene was slowly added within 20 min. Then the reaction mixture was gently heated to reflux temperature and stirred at this temperature for 48 hours. The solvent was then removed using a rotation evaporator and the residue was chromatographed over $SiO_2$ in hexane/EtOAc=9:1.

3.5 g of a semicrystalline product was isolated. UV 308 nm (133230), m.p. 86–87° C.

d) Measurement of solubility in Cétiol LC (cocoyl caprylate caprate) and Crodamol DA (diisopropyl adipate).

Oversaturated solutions of 2,4,6-tri-anilino-p-{carbo-4'-(1,1,3,3,3-pentamethyl disiloxanyl)-1'-butyloxy}-1,3,5-triazine in the above solvents were prepared and treated in an ultrasound bath for five minutes. After standing over night at 25° C. the solution was filtered through a microfilter (Millipore, pore size 0.5·m), followed by UV measurement in $CH_2Cl_2$. The extinctions were compared with the extinction of the pure compound. The solubilities were found to be 11.2% in Cétiol LC and >26% in Crodamol DA.

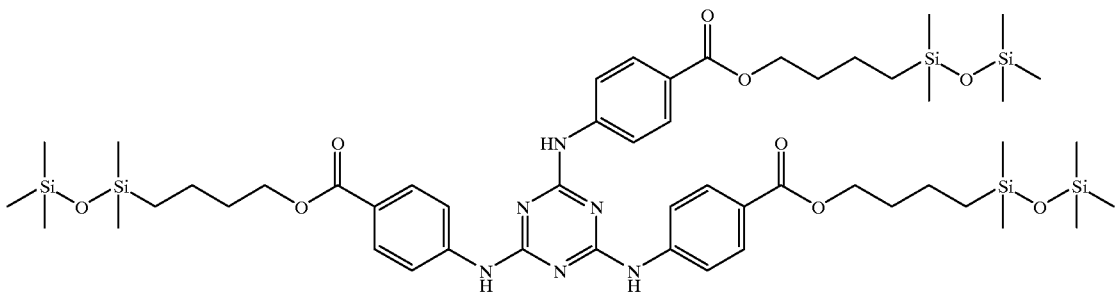

Examples 2 to 5 were prepared following the procedure as described in Example 1.

EXAMPLE 2

Preparation of 2,4,6-tri-anilino-p-{carbo-4'-(1,1,1,3,5,5,5-heptamethyl trisiloxanyl)-1'-butyloxy}-1,3,5-triazine.

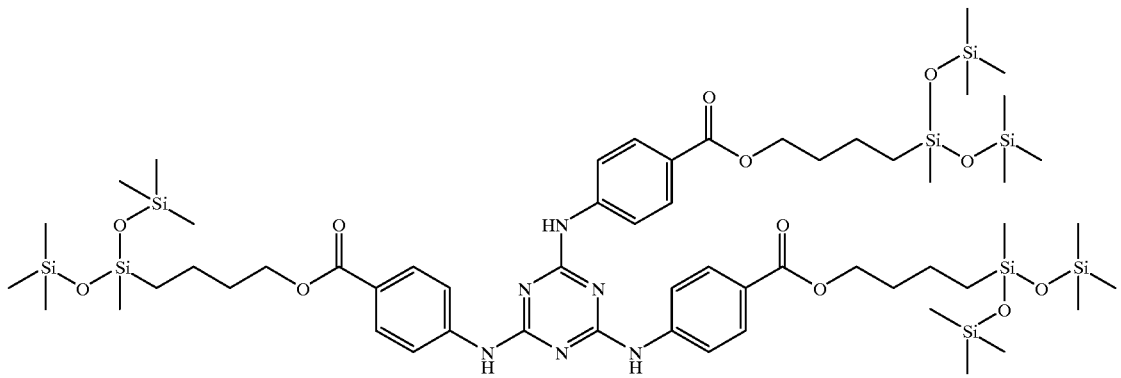

a) First step: preparation of 4-(1,1,1,3,5,5,5-heptamethyl trisiloxanyl)-1-butanol using 1,1,1,3,5,5,5-heptamethyl trisiloxane. After distillation at 74–78° C./0.1×10² Pa 83% of a liquid product was obtained.

b) Second step: preparation of 4-aminobenzoic acid 4-(1,1,1,3,5,5,5-heptamethyl trisiloxanyl) butyl ester by reacting 4-(1,1,1,3,5,5,5-heptamethyl trisiloxanyl)-1-butanol with ethyl 4-aminobenzoic acid ester. After chromatography over $SiO_2$ in hexane/EtOAc=1.1 and evaporation of the starting material, a clear yellow oil was obtained in 43% yield.

c) Third step: preparation of 2,4,6-tri-anilino-p-{carbo-4'-(1,1,1,3,5,5,5-heptamethyl trisiloxanyl)-1'-butyloxy}-1,3,5-triazine by heating to reflux 4-aminobenzoic acid 4-(1,1,1,3,5,5,5-heptamethyl trisiloxanyl) butyl ester and cyanuric acid chloride. After chromatography 37% of the product was obtained. UV 308 nm (120459), m.p. 115–118° C.

d) Measurement of solubility in Cétiol LC and Crodamol DA: 19.1% in Cétiol LC and 35.5% in Crodamol DA.

EXAMPLE 3

Preparation of 2,4,6-tri-anilino-p-{carbo-2'-methyl-3'-(1,1,3,3,3-pentamethyl disiloxanyl)-1'-propyloxy}-1,3,5-triazine.

instead of 3-butene-1-ol. After distillation at 105° C./40×10² Pa 81% of a liquid product was obtained.

b) Second step: preparation of 4-aminobenzoic acid 2-methyl-3-(1,1,3,3,3-pentamethyl disiloxanyl) propyl ester by reacting 3-(1,1,3,3,3-pentamethyl disiloxanyl)-2-methyl-1-propanol. A clear yellow oil was obtained in 27% yield.

c) Third step: preparation of 2,4,6-tri-anilino-p-{carbo-2'-methyl-3'-(1,1,3,3,3-pentamethyl disiloxanyl)-1'-propyloxy}-1,3,5-triazine by heating to reflux 4-aminobenzoic acid 2-methyl-3-(1,1,3,3,3-pentamethyl disiloxanyl) propyl ester and cyanuric acid chloride. After chromatography 33% of the product was obtained. UV 308 nm (109184), m.p. 118–120° C.

d) Measurement of solubility in Cétiol LC and Crodamol DA: 16.8% in Cétiol LC and >34% in Crodamol DA.

EXAMPLE 4

Preparation of 2,4,6-tri-anilino-p-{carbo-5'-(1,1,3,3,3-pentamethyl disiloxanyl)-1'-pentyloxy}-1,3,5-triazine.

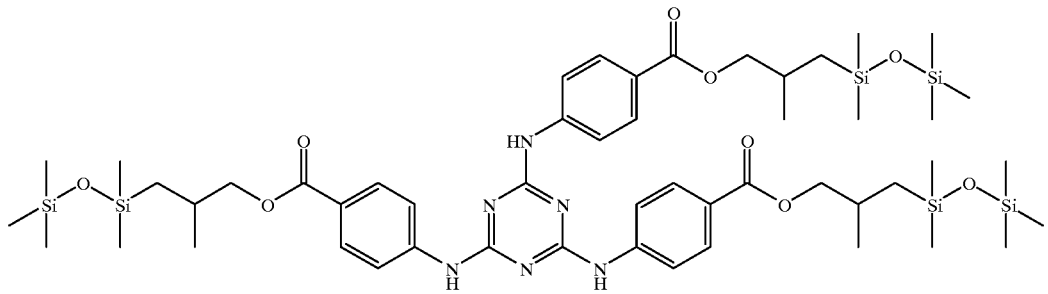

a) First step: preparation of 3-(1,1,3,3,3-pentamethyl disiloxanyl)-2-methyl-1-propanol using 2-methallyl alcohol

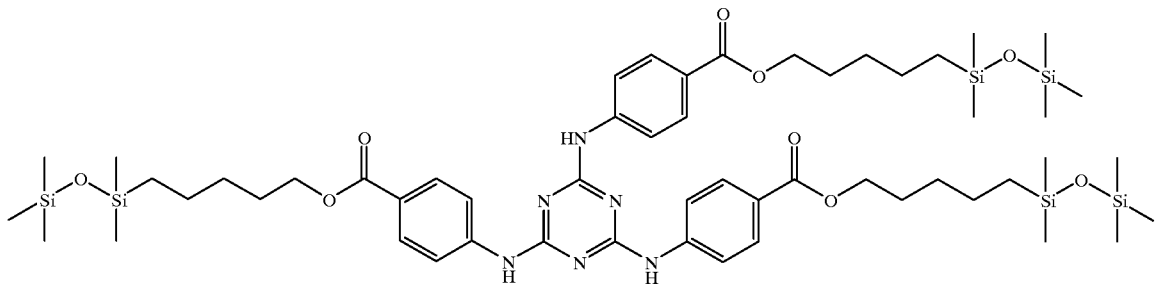

a) First step: preparation of 5-(1,1,3,3,3-pentamethyl disiloxanyl)-1-pentanol by using 4-penten-1-ol instead of 3-butene-1-ol. After distillation at 124–125° C./39×10² Pa 88% of a liquid product was obtained.

b) Second step: preparation of 4-aminobenzoic acid 5-(1,1,3,3,3-pentamethyl disiloxanyl) pentyl ester by reacting 5-(1,1,3,3,3-pentamethyl disiloxanyl)-1-pentanol instead of 4-(1,1,3,3,3-pentamethyl disiloxanyl)-1-butanol. A clear yellow oil was obtained in 63% yield.

c) Third step: preparation of 2,4,6-tri-anilino-p-{carbo-5'-(1,1,3,3,3-pentamethyl disiloxanyl)-1'-pentyloxy}-1,3,5-triazine by heating to reflux 4-aminobenzoic acid 5-(1,1,3,3,3-pentamethyl disiloxanyl) pentyl ester and cyanuric acid chloride. After chromatography 20% of the product was obtained. UV 308 nm (137085), m.p. 119.5–121.5° C.

d) Measurement of solubility in Cétiol LC and Crodamol DA: 6.2% in Cétiol LC and 13% in Crodamol DA.

EXAMPLE 5

Preparation of 2,4,6-tri-anilino-p-{carbo-3'-(1,1,3,3,3-pentamethyl disiloxanyl )-1'-propyloxy}-1,3 5-triazine.

a) First step: preparation of 3-(1,1,3,3,3-pentamethyl disiloxanyl)-1-propanol using allyl alcohol instead of 3-butene-1-ol. After distillation at 99–101° C./41×10² Pa 85% of a liquid product was obtained.

b) Second step: preparation of 3-aminobenzoic acid 3-(1,1,3,3,3-pentamethyl disiloxanyl) propyl ester by reacting 3-(1,1,3,3,3-pentamethyl disiloxanyl)-1-propanol. A clear yellow oil was obtained in 14% yield.

c. Third step: preparation of 2,4,6-tri-anilino-p-{carbo-3'-(1,1,3,3,3-pentamethyl disiloxanyl)-1'-propyloxy}-1,3,5-triazine by heating to reflux 3-aminobenzoic acid 3-(1,1,3,3,3-pentamethyl disiloxanyl) propyl ester and cyanuric acid chloride. After chromatography 32% of the product was obtained. UV 308 nm (111664), m.p. 125–127° C.

d. Measurement of solubility in Cétiol LC and Crodamol DA: 4.3% in Cétiol LC and >16% in Crodamol DA.

EXAMPLE 6

Preparation of 2,4,6-tri-anilino-p-{carbo-4'-(triethly silyl)-1'-but-3-enyloxy}-1,3,5-triazine

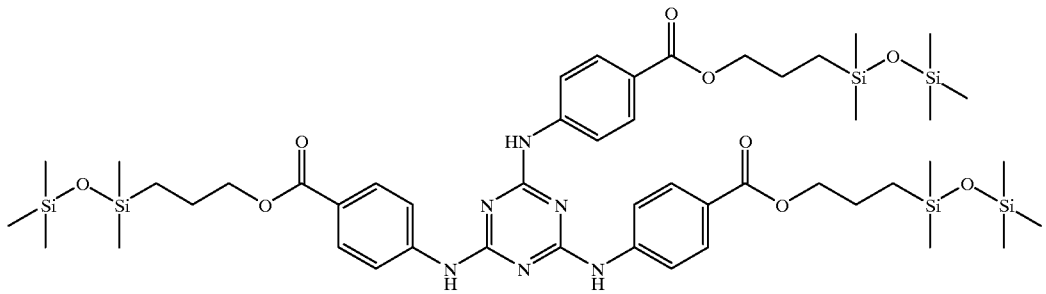

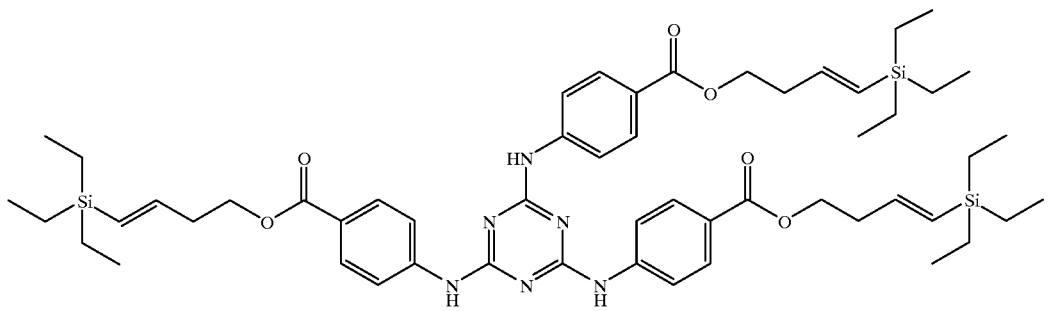

a) First step: preparation of 4-(triethylsilyl)-1-but-3-enol

A 50 ml reaction flask was charged with 1 butene-3-ol and a catalytic amount of bis(1,5-cyclooctadien)-di-Rh(I)-dichloride and triphenylphosphine under inert atmosphere. Triethylsilane was slowly added through a dropping funnel. The reaction mixture was stirred at room temperature for 72 h. 86% of a yellow liquid was obtained.

b) Second step: preparation of 4-aminobenzoic acid-(triethylsilyl) 1-but-3-enylester by reacting 4-aminobenzoic acid ester and 4-(triethylsilyl)-1-but-3-enol. Yield: 69% of a clear liquid.

c) Third step: preparation of 2,4,6-tri-anilino-p-{carbo-4'-(triethly silyl)-1'-but-3-enyloxy}-1,3,5-triazine.

EXAMPLE 7

Example 7 was prepared analog to Example 6.

Preparation of 2,4,6-tri-anilino-p-{carbo-4'-(triethyl silyl)-1'-butyloxy}-1,3,5-triazine a) First step: preparation of 4-(triethylsilyl)-1butanol.

b) Second step: preparation of 4-aminobenzoic acid-(triethylsilyl) butylester.

c) Third step: preparation of 2,4,6-tri-anilino-p-{carbo-4'-(triethyl silyl)-1'-butyloxy}-1,3,5-triazine.

EXAMPLE 8

Preparation of 2,4,6-tri-anilino-(p-carboethoxy)-1,3,5-triazine as a reference compound without any silyl groups.

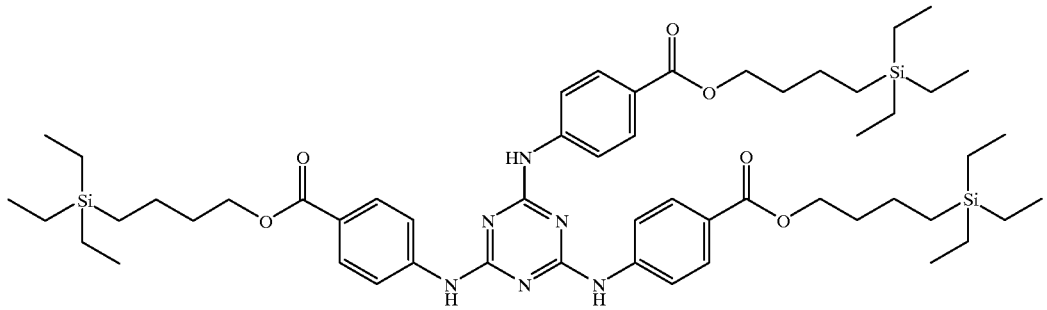

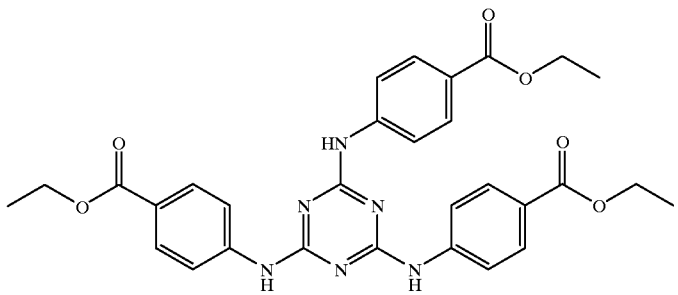

A 750 ml reaction flask was charged with 13.9 g of ethyl-p-amino-benzoate dissolved in 300 ml of p-cymene. A solution of 4.85 g of cyanuric acid chloride in 150 ml of p-cymene was slowly added within 20 min. A white suspension was formed. Then the reaction mixture was gently heated to reflux temperature (170° C.) and stirred at this temperature for 20 h. The reaction mixture was cooled to 0° C., filtered and the residue was washed with MTBE and recrystalised in toluene to yield 12.3 g (82%) of white crystals. UV 308 nm (133,374), m.p. 218–220° C., which predicted a low solubility.

Measurement of solubility in Cétiol LC and Crodamol DA:

The solubility's were determined as described in Example 1 and were found to be 0.02% in Cétiol LC and 0.2% in Crodamol DA.

EXAMPLE 9

Measurement of solubility of UVINUL T-150 in Cétiol LC and Crodamol DA for comparison:

The solubilities were determined for the commercial product Uvinul T-150, as a reference, as described in Example 1. UVINUL T-150 was the best soluble compound within the known series. The solubilities were found to be 3.7–4.2% in Cétiol LC and 10% in Crodamol DA, which was lower then for the examples is according to the invention. The m.p. was 126–127.5° C.

EXAMPLE 10

Preparation of 2,4,6-tri-anilino-p-{carbo-7'-(triethyl silyl)-4'-oxa-heptyloxy}-1,3,5-triazine.

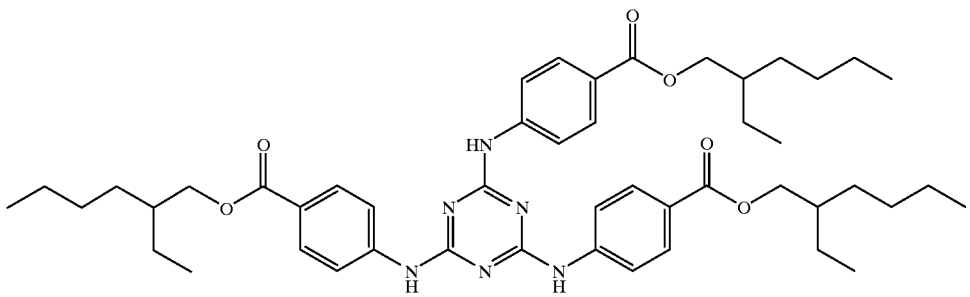

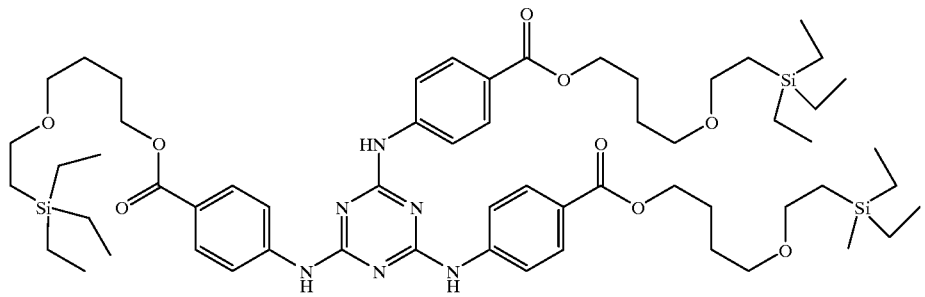

a) 4-(2-Triethylsilanyl-ethoxy)-butanol:

A 50 ml reaction flask was charged with 11.6 ml (100 mmol) of 1,4-butanediol-mono vinylether and a catalytic amount of divinyl-tetramethyl disiloxane platinum complex under inert atmosphere and heated to 60° C. 10.4 g (90 mmol) of triethylsilane was slowly added through a dropping funnel. The exothermic reaction mixture was stirred at 75° C. for 18 hours, followed by distillation at 105 to 107° C./0.2 mbar over a 10 cm Vigreux column.

Yield 15.2 g (66% of theoretical) of a clear liquid. Purity 98.7% according gas chromatography.

b) 4-Aminobenzoic acid 4-(2-triethylsilanyl-ethoxy)-butyl ester:

The same reaction was performed as in example 1b, using the product of the above reaction instead of 4-(1,1,3,3,3-pentamethyl disiloxanyl)-1-butanol. A clear yellow oil was received in 65% yield after chromatography.

c) 2,4,6-Tri-anilino-p-{carbo-7'-(triethyl silyl)-4'-oxa-heptyloxy}-1,3,5-triazine.

The reaction procedure of example 1c was repeated using the p-amino benzoic acid ester received above instead of p-aminobenzoic acid 4-(pentamethyl disiloxanyl) butyl ester. After chromatography 79% of the product is obtained. UV 308 nm (ε=117,723), m.p. 79–81° C.

d) Measurement of solubility in cosmetic solvents:

The solubilities were determined as described in example 1 and were found to be 31% in Cétiol LC and 45% in Crodamol DA.

EXAMPLE 11

Preparation of 2,4,6-tri-anilino-p-{carbo-7'-(1,1,3,3,3-pentamethyl disiloxanyl )-4'-oxa-heptyloxy}-1,3,5-triazine.

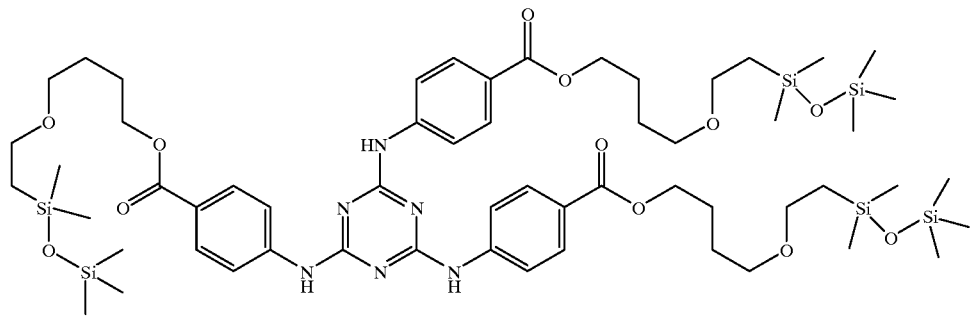

a) 7-(1,1,3,3,3-Pentamethyl-disiloxanyl)-4-oxa-heptan-1-ol:

A 50 ml reaction flask was charged with 16 ml of 1,4-butanediol-vinylether and a catalytic amount of divinyl-tetramethyl disiloxane platinum complex under inert atmosphere and heated to 60° C. 22.8 ml of pentamethyl disiloxane was slowly added through a dropping funnel. The reaction mixture was stirred at 75 to 80° C. for 18 hours, followed by distillation at 85 to 87° C./0.2 mbar over a 10 cm column. Yield 29 g (85% of theoretical) of a clear liquid.

b) 4-Nitrobenzoic acid 7-(1,1,3,3,3-pentamethyl-disiloxanyl)-4-oxa-heptyl ester:

A 100 ml reaction flask was charged with 20 g of the above silylated alcohol in 34 ml of pyridine and vigorously stirred. 22.5 g of p-nitrobenzoic acid chloride was slowly added within 20 min. The reaction mixture was heated to 60° C. and stirred for one hour. Then it was poured in ice water and extracted with $CH_2Cl_2$. The combined organic phases were washed with 1N HCl and saturated $NaHCO_3$ solution, dried over $Na_2SO_4$ and concentrated to yield 20.2 g (65%) of a yellow liquid. MS: 370, 298, 150, 147, 120(100%).

c) 4-Aminobenzoic acid 7-(1,1,3,3,3-pentamethyl-disiloxanyl)-4-oxa-heptyl ester:

A 600 ml hydrogenation autoclave was charged with 20 g of the above ester in 280 ml of methanol and 0.7 g of acetic acid and 3 g of Raney Ni catalyst. This mixture was hydrogenated for 18 hours at room temperature and a pressure of 100 psi. Then the mixture was filtered, distributed between ethyl acetate and water and the organic phase was concentrated to yield 93% of a yellow liquid. MS: 383(M$^+$), 340, 268, 208, 147, 120(100%).

d) 2,4,6-Tri-anilino-p-{carbo-7'-(1,1,3,3,3-pentamethyl disiloxanyl)-4'-oxa-heptyloxy}-1,3,5-triazine.

The reaction procedure of example 1c was repeated using p-amino benzoic acid ester received above instead of p-aminobenzoic acid 4-(pentamethyl disiloxanyl) butyl ester. After chromatography 60% of the product is obtained. UV 308 nm ($\epsilon$=124,248), m.p. 74–76° C.

e) Measurement of solubility in cosmetic solvents:

The solubilities were determined as described in example 1 and were found to be 28% in Cétiol LC and 29.4% in Crodamol DA.

EXAMPLE 12

Preparation of 2,4-di-anilino-p-carbo-(2'-ethyl-hexyloxy)-6-anilino-p-{carbo-7'-(1,1,3,3,3-pentamethyl disiloxanyl)-4'-oxa-heptyloxy}-1,3,5-triazine.

After 18 hours the reaction mixture was distributed between water and ethyl acetate. The organic phases were dried and concentrated to yield 2.6 g of a crystalline product which was chromatographed on silica gel in hexane:ethyl acetate= 7:3.

1.8 g (56%) of a white crystalline material was isolated. MS: 609 (M$^+$), 497, 385 (100%).

b) 2,4-Di-anilino-p-carbo-(2'-ethyl-hexyloxy)-6-anilino-p-{carbo-7'-(1,1,3,3,3-pentamethyl disiloxanyl)-4'-oxa-heptyloxy)-1,3,5-triazine.

A 25 ml reaction flask was charged with 0.61 g of the above di-anilino-triazine in 15 ml of toluene and heated to 65° C. A solution of 0.38 g of 4-aminobenzoic acid 7-(1,1, 3,3,3-pentamethy-disiloxanyl)-4-oxa-heptanyl ester (see example 11c) in 3 ml of toluene was added and the reaction was stirred for 7 hours at 75° C. Then the reaction mixture was concentrated and chromatographed on silica gel in hexane:ethyl acetate=7:3 to yield 46% of a white crystalline product. UV 308 nm ($\epsilon$=112,526), m.p. 107–109° C.

c) Measurement of solubility in cosmetic solvents:

The solubilities were determined as described in example 1 and were found to be 22% in Cétiol LC and >36% in Crodamol DA.

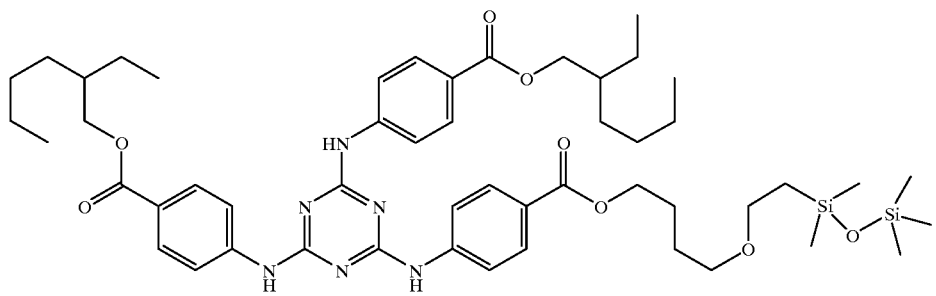

a) 2,4-Di-anilino-p-carbo-(2'-ethyl-hexyloxy)-6-chloro-1, 3,5-triazine.

A 100 ml reaction flask was charged with 0.92 g of cyanuric acid chloride in 50 ml of THF. A solution of 1.2 g of 2-ethyl-hexyl p-aminobenzoate and 0.85 ml of diisopropyl ethylamine in 25 ml THF was slowly added at 0° C. The reaction was slowly heated to 45° C. and again a solution of 1.2 g of 2-ethyl-hexyl p-aminobenzoate and 0.85 ml of diisopropyl ethylamine in 25 ml THF was slowly added.

EXAMPLE 13

Preparation of 2,4-di-anilino-p-carbo-(2'-ethyl-hexyloxy)-6-anilino-p-{carbo-7'-(1,1,1,3,5,5,5-heptamethyl trisiloxanyl)-4'-oxa-heptyloxy}-1,3,5-triazine.

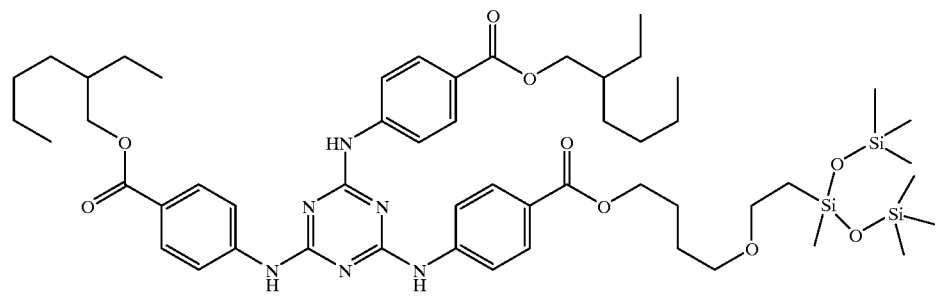

a) 7-(1,1,1,3,5,5,5-Heptamethyl trisiloxanyl)-4-oxa-heptanol:

A 50 ml reaction flask was charged with 11.6 g of 1,4-butanediol-vinylether and a catalytic amount of divinyl-tetramethyl disiloxane platinum complex under inert atmosphere and heated to 80° C. 20 g of heptamethyl trisiloxane was slowly added through a dropping funnel. The reaction mixture was stirred at 85° C. for 4 hours, followed by distillation at 110 to 112° C./0.25 mbar over a 10 cm column. Yield 22.1 g (73% of theoretical) of a clear liquid.

b) 4-Nitrobenzoic acid 7-(1,1,1,3,5,5,5-heptamethyl trisiloxanyl)-4-oxa-heptyl ester:

A 25 ml reaction flask was charged with 8 g of the above silylated alcohol in 10.5 ml of pyridine and vigorously stirred. 7 g of p-nitrobenzoic acid chloride was slowly added within 20 min. The reaction mixture was heated to 60° C. and stirred for one hour. Then it was poured into ice water and extracted three times with $CH_2Cl_2$. The combined organic phases were washed with 1N HCl and saturated $NaHCO_3$ solution, dried over $Na_2SO_4$ and concentrated to yield 9.9 g (86%) of a yellow liquid.

c) 4-Aminobenzoic acid 7-(1,1,1,3,5,5,5-heptamethyl trisiloxanyl)-4-oxa-heptyl ester:

A 300 ml hydrogenation autoclave was charged with 9.7 g of the above ester in 115 ml of methanol and 0.3 g of acetic acid and 1.2 g of Raney Ni catalyst. This mixture was hydrogenated for 18 hours at room temperature and a pressure of 100 psi. Then the mixture was filtered, distributed between ethyl acetate and water and the organic phase was concentrated to yield 8.3 g (91%) of a yellow liquid. MS: 457($M^+$), 342, 268, 221, 208, 137, 120(100%).

d) 2,4-Di-anilino-p-carbo-(2'-ethyl-hexyloxy)-6-anilino-p-{carbo-7'-(1,1,1,3,5,5,5-hepta-methyl trisiloxanyl)-4'-oxa-heptyloxy}-1,3,5-triazine.

A 25 ml reaction flask was charged with 0.85 g of 2,4-di-anilino-p-carbo-(2'-ethyl-hexyloxy)-6-chloro-1,3,5-triazine (preparation was described in example 12a) dissolved in 15 ml of toluene and heated to 65° C. A solution of 0.7 g of 4-aminobenzoic acid 7-(1,1,1,3,5,5,5-heptamethyl trisiloxanyl)-4-oxa-heptanyl ester (see above) in 3 ml of toluene was added and the reaction was stirred for 7.5 hours at 75° C. Then the reaction mixture was concentrated and chromatographed on silica gel in hexane:ethyl acetate=7:3 to yield 1.13 g (79%) of a white crystalline product. UV 308 nm ($\epsilon$=105,587), m.p. 103–105° C.

e) Measurement of solubility in cosmetic solvents:

The solubilities were determined as described in example 1 and were found to be 27% in Cétiol LC and >47% in Crodamol DA.

EXAMPLE 14

Preparation of 2,4-di-anilino-p-carbo-(2'-ethyl-hexyloxy)-6-amino{N-(-2'-(1,1,1,3,5,5,5-heptamethyl trisiloxanyl)-allyl)-n-benzamidyl}-1,3,5-triazine.

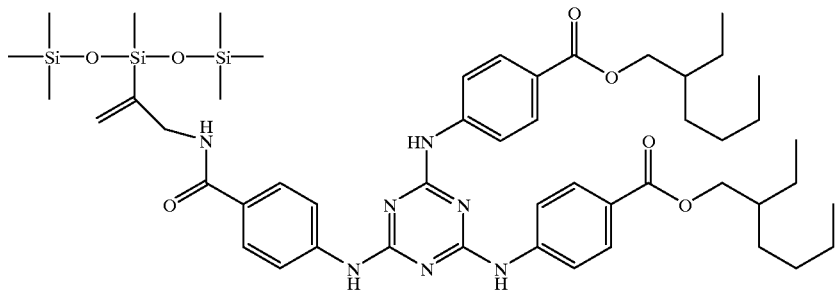

a) 4-Nitrobenzoic acid propargylamide:

A 500 ml reaction flask is charged with 19.8 ml of propargylamine and 62 ml of triethylamine in 150 ml of methyl-tert.butyl ether (MTBE). 55.2 g of p-nitrobenzoic acid chloride is dissolved in 100 ml of MTBE and slowly added within 20 min. The reaction mixture is vigorously stirred for 90 min. and then heated to 60° C. for further 30 min. Then it is filtered and the residue washed with water, again filtered and recrystallised in acetonitrile to yield 40.7 g of yellow crystals.

b) 4-Aminobenzoic acid propargylamide:

A 1 l reaction flask was charged with 33.5 g of 4-nitrobenzoic acid propargylamide dissolved in 410 ml of methanol and 410 ml of concentrated aq. hydrochloric acid. 81.8 g of tin powder was added and the reaction was heated to 40° C. for 165 min. Then the reaction mixture was poured in a solution of 410 g of NaOH in 1640 ml of ice water and the methanol was distilled off and filtered when hot to remove the inorganic material. The product crystallised from this solution. It was recrystallised from ethanol/water to yield 21.5 g (75%) of the desired material. m.p. 122–125° C.

c) 4-(4,6-Dichloro-(1,3,5)triazin-2-ylamino)-N-(propargyl-p-benzamide.

A 75 ml reaction flask was charged with a cooled solution of 1.85 g of cyanuric acid chloride and 0.88 g of $NaHCO_3$ in 20 ml of acetone. A solution of 1.77 g of 4-aminobenzoic acid propargylamide in 6 ml of acetone was slowly added at 0° C. The yellowish suspension was stirred for 30 min. Then 9 ml of water was added and the product was filtered off to yield 2.5 g of a yellowish powder. MS: 322($M^+$), 321, 292, 267(100%).

d) 2,4-Di-anilino-p-carbo-(2'-ethyl-hexyloxy)-6-amino-{N-(propargyl)-p-benzamidyl}-1,3,5-triazine.

A 25 ml reaction flask was charged with 1.04 g of 2-ethyl-hexyl p-aminobenzoate and 0.64 g of 4-(4,6-dichloro-(1,3,5)triazin-2-ylamino)-N-(propargyl-p- benzamide received above dispersed in 12 ml of Xylene and refluxed for six hours. The reaction mixture was cooled to 0° C. and the product was filtered off and once more recrystallised in toluene. 0.98 g of a slightly yellow powder was obtained. UV 306 nm (111,436), MS: 747(100%, M$^+$).

e) 2,4-Di-anilino-p-carbo-(2'-ethyl-hexyloxy)-6-amino (N-(-2'-(1,1,1,3,5,5,5-heptamethyl trisiloxanyl )-allyl)-p-benzamidyl}-1,3,5-triazine.

A 25 ml reaction flask was charged with 1.23 g of the triazine received above in 19 ml of toluene, 0.45 g of 1,1,1,3,5,5,5-heptamethyl trisiloxane and a catalytic amount of divinyl-tetramethyl disiloxane platinum complex under inert atmosphere. The reaction mixture was heated to 95° C. for five days, washed with water, concentrated and chromatographed in hexane ethyl acetate=7:3. 0.25 g of off white crystals were isolated. UV 306 nm ($\epsilon$=106,517), m.p. 76–80° C.

f) Measurement of solubility in cosmetic solvents:

The solubilities were determined was described in example 1 and were found to be >24% in Cétiol LC and >37% in Crodamol DA.

EXAMPLE 15

Preparation of a polysiloxane which corresponds in its statistical mean to the following formula:

4-nitrobenzoic acid 3-propargyloxy propylamide and heating only for 15 min. to 35° C. The liquid part of the reaction mixture was poured into water and extracted with $CH_2Cl_2$ until no product can be traced in the water phase. After concentration a yellow honey is obtained in 97% yield, the structure of which was proved by NMR. MS: 232(M$^+$), 193, 120(100%).

d) 4-(4,6-Dichloro-(1,3,5)triazin-2-ylamino)-N-(3-propargyloxy-propyl-p-benzamide.

The reaction described in example 14c was repeated using 4-aminobenzoic acid 3-propargyloxy propylamide instead of 4-aminobenzoic acid propargylamide. The product was filtered off to yield an off white powder in 65.5%. MS: 379(M$^+$), 342, 340, 269, 267(100%).

e) 2,4-di-Anilino-p-carbo-(2'-ethyl-hexyloxy)-6-amino-{N-(3-propargyloxy-propyl)-p-benzamidyl}-1,3,5-triazine.

The reaction described in example 14d was repeated using 4-(4,6-dichloro-(1,3,5)triazin-2-ylamino)-N-(3-propargyloxy-propyl-p-benzamide described above as starting material. The raw product was chromatographed in hexane/ethyl acetate=1:1. A yellowish powder was obtained in 85% yield. UV 306 nm ($\epsilon$=104,380), m.p. 78–81° C.

f) Polysiloxane grafted triazine.

A 25 ml reaction flask was charged with 0.4 g of the triazine received above in 10 ml of toluene, 0.55 g of

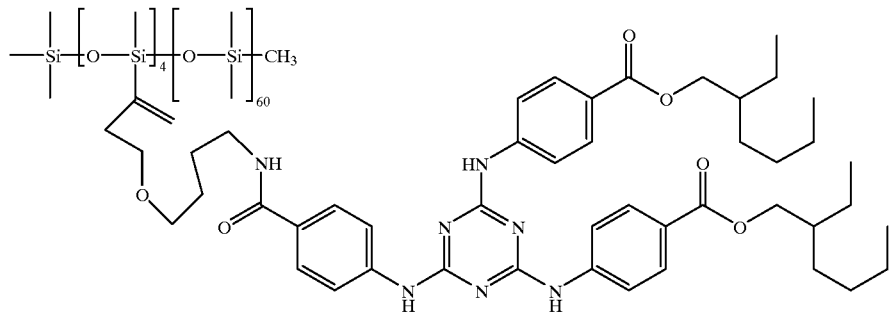

a) 4-Nitrobenzoic acid-3-propanolamide:

The reaction described in example 14a was repeated using 2.5 equivalents of 3-amino propanol instead of propargyl amine and triethylamine. The reaction mixture was poured on water and seven times extracted with ethyl acetate. The combined ethyl acetate phases were dried with $Na_2SO_4$ and concentrated to yield 73% of a crystalline product, which was identified by NMR.

b) 4-Nitrobenzoic acid 3-propargyloxy propylamide:

A 100 ml reaction flask was charged with 10 g of 4-nitrobenzoic acid 3-propargyloxy propylamide dissolved in 70 ml of THF and 5.25 g of Potassium tert. butoxyde and treated with 5.1 ml of propargyl bromide. After 50 min. the reaction mixture was heated to 60° C. for five hours and then distributed between water and ethyl acetate. The combined organic phases were concentrated and chromatographed in hexane/ethyl acetate=9:1 to yield 2.1 g of a yellow crystalline material, which again is identified by NMR.

c) 4-Aminobenzoic acid 3-propargyloxy propylamide:

The reaction described in example 14b was repeated using 4-nitrobenzoic acid 3-propargyloxy propylamide instead of polysiloxane Ae-151 of Wacker-Chemie GmbH. and a catalytic amount of divinyl-tetramethyl disiloxane platinum complex under inert atmosphere. The reaction mixture was heated to 100° C. for four days, washed with water/methanol=1:10, concentrated and chromatographed in hexane ethyl acetate=7:3. 0.9 g of yellowish liquid was isolated, which is freely miscible with Cétiol LC or Crodamol DA. WV 306 nm (E=524).

EXAMPLE 16

Preparation of a O/W sunscreen lotion UV-B and UV-A:

Broad spectrum sunscreen lotion containing 2% of a compound of Ex. 1.

| Recipe: % | compound | INCI name |
|---|---|---|
| Part A: | | |
| 2% | PARSOL MCX | Octyl methoxycinnamate |
| 2% | Product of Example 1 | |
| 3% | PARSOL 1789 | 4-tert.Butyl-4'methoxydibenzoyl methane |
| 12% | CETIOL LC | Coco-caprylate/caprate |
| 4% | DERMOL 185 | Isostearyl neopentanoate |
| 0.25% | | Diethyleneglycolmonostearate |
| 1% | | Cetylalcohol |
| 0.25% | MPOB/PPOB | Methyl-propylparaben |
| 0.1% | EDETA BD | EDTA-disodium salt |
| 1% | AMPHISOL DEA (Giv.) | Diethanolamine cetylphosphate |
| Part B: | | |
| 20% | PERMULENE TR-1 (+%) | Acrylate $C_{10}$–$C_{30}$ Alkylacrylate-cross polymer |
| 48.6% | | water deion. |
| 5% | | 1,2-Propanediol |
| 0.8% | | Potassium hydroxide (10%) |

Part A was heated in a reactor to 85° C. Part B was slowly added within 10 min., followed by addition of KOH, cooling and degassing of the emulsion.

What is claimed is:

1. A compound of the formula

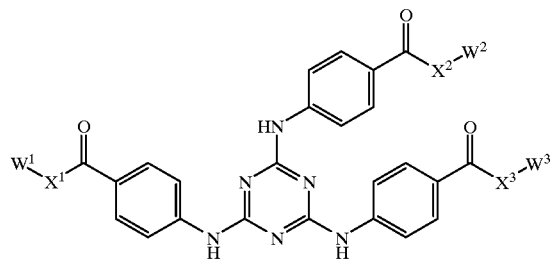

wherein $W^1$, $W^2$, and $W^3$ each independently signifies $C_1$–$C_{20}$ alkyl or SpSil;

$X^1$, $X^2$, and $X^3$ each independently signifies O or NH;

Sp is a spacer group selected from the group consisting of a $C_3$–$C_{12}$ divalent alkyl and an alkylene chain;

Sil is selected from the group consisting of (a) $SiR^1R^2R^3$, wherein $R^1$, $R^2$, and $R^3$ each independently signify $C_1$–$C_6$ alkyl, $C_1$–$C_6$ alkoxy, or phenyl; (b) $SiR^{10}{}_m(OSiR^{10}{}_3)_n$, wherein m=0, 1, or 2, n=3, 2, or 1, and m+n=3, or a compound of the formula IIa, IIa', or IIb

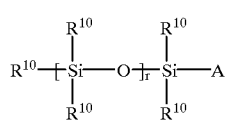

IIa

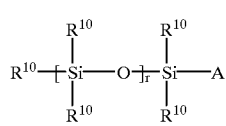

IIa'

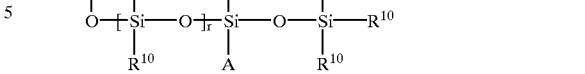

IIb wherein

A signifies a bond to Sp, $R^{10}$ is selected from the group consisting of $C_1$–$C_6$ alkyl and phenyl, and r signifies 1 to 9; and (c) a compound selected from the group consisting of a compound of formula IIIa and a compound of formula III b

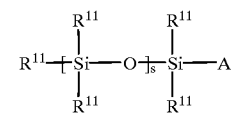

IIIa

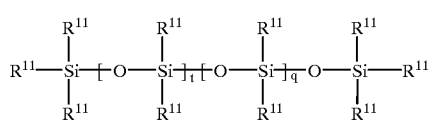

IIIb wherein

A signifies a bond to Sp, $R^{11}$ is selected from the group consisting of $C_1$–$C_6$ alkyl and phenyl, s signifies 4 to 250, t signifies 5 to 250, and q signifies 1 to 30;

with the proviso that at least one of $W^1$, $W^2$ and $W^3$ signifies SpSil.

2. The compound according to claim 1, wherein $W^1$, $W^2$ and $W^3$ signify SpSil, or $W^1$ and $W^2$ signify $C_1$–$C_{20}$ alkyl and $W^3$ signifies SpSil.

3. The compound according to claim 1, wherein $X^1$, $X^2$ and $X^3$ signify oxygen, or $X^1$ and $X^2$ signify oxygen and $X^3$ signifies NH.

4. The compound according to claim 1, wherein the spacer is a $C_3$–$C_{12}$ alkylene.

5. The compound according to claim 1, wherein the spacer is a $C_3$–$C_{12}$ alkylene chain with at least one carbon atom being replaced by an oxygen atom.

6. The compound according to claim 4, wherein the spacer group signifies —$(CH_2)_3$—, —$(CH_2)_4$—, —$(CH_2)_5$—, —(CH)($CH_3$)—($CH_2$)—, —$(CH_2)_2$—CH═CH—, —C(═$CH_2$)—$CH_2$—, —C(═$CH_2$)—$(CH_2)_2$—O—$(CH_2)_4$—, $(CH_2)_4$—O—$(CH_2)_2$—.

7. The compound according to claim 5, wherein the spacer group signifies —$(CH_2)_3$—, —$(CH_2)_4$—, —$(CH_2)_5$—, —($CH_2$)($CH_3$)—($CH_2$)—, —$(CH_2)_2$—CH═CH—, —C(═$CH_2$)—$CH_2$—, —C(═$CH_2$)—$(CH_2)_2$—O—$(CH_2)_4$—, $(CH_2)_4$—O—$(CH_2)_2$—.

8. The compound according to claim 1, wherein the spacer group signifies 3-propylene, 2-propylene, 2-propen-2-ylene, 2-propen-3-ylene, 2-methyl-3-propylene, 2-methyl-3-propenylene, 3-butyl, 4-butylene, 3-but-3-enylene, 4-but-3-enylene, 4-pentylene, 5-pentylene, 4-pent-4-enylene, 5-pent-4-enylene, 4- or 5-(3-methyl)penta-2,4-dienylene, 6-hexylene, 12-dodecylene or 11-dodecen-11-ylene.

9. The compound according to claim 1, wherein the silane moiety signifies a group SiR$^1$R$^2$R$^3$, wherein R$^1$, R$^2$ and R$^3$ each independently signify C$_1$–C$_6$ alkyl, C$_1$–C$_6$ alkoxy or phenyl.

10. The compound according to claim 1, wherein the silane moiety signifies —Si(CH$_3$CH$_3$)$_3$— or —Si(CH$_2$—CH$_2$—CH$_3$)$_3$.

11. The compound according to claim 1, wherein s has a value of from 5 to 150.

12. The compound according to claim 1, wherein t has a value of from 5 to 150.

13. The compound according to claim 1, wherein t has a statistical mean of about 60.

14. The compound according to claim 1, wherein q has a value of from 2 to 10.

15. The compound according to claim 1, wherein q has a statistical mean of about 4.

16. The compound according to claim 9, wherein R$^{10}$ and R$^{11}$ signify C$_1$–C$_6$ alkyl.

17. The compound according to claim 16, wherein R$^{10}$ and R$^{11}$ signify C$_1$–C$_4$ alkyl.

18. The compound according to claim 17, wherein R$^{10}$ and R$^{11}$ signify methyl.

19. The compound according to claim 10, wherein R$^{10}$ and R$^{11}$ signify C$_1$–C$_6$ alkyl.

20. The compound according to claim 19, wherein R$^{10}$ and R$^{11}$ signify C$_1$–C$_4$ alkyl.

21. The compound according to claim 20, wherein R$^{10}$ and R$^{11}$ signify methyl.

22. A process for the manufacture of a compound of formula I

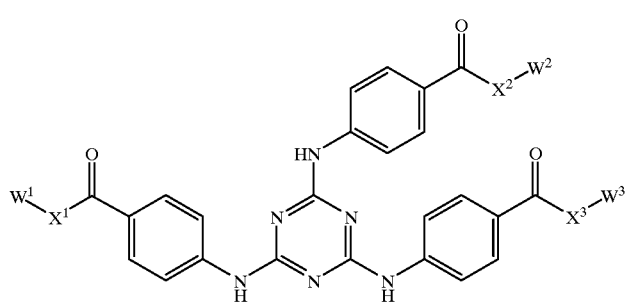

whererin

W$^1$, W$^2$, and W$^3$ each independently signifies C$_1$–C$_{20}$ alkyl or SpSil;

X$^1$, X$^2$, and X$^3$ each independently signifies O or NH;

Sp is a spacer group selected from the group consisting of a C$_3$–C$_{12}$ divalent alkyl and an alkylene chain;

Sil is selected from the group consisting of (a) SiR$^1$R$^2$R$^3$, wherein R$^1$, R$^2$, and R$^3$ each independently signify C$_1$–C$_6$ alkyl, C$_1$–C$_6$ alkoxy, or phenyl; (b) SiR$^{10}_m$(OSiR$^{10}_3$)$_n$, wherein m=0, 1, or 2, n=3, 2, or 1, and m+n=3, or a compound of the formula IIa, IIa', or IIb

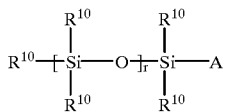

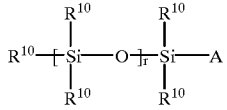

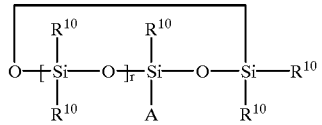

wherein

A signifies a bond to Sp,

R$^{10}$ is selected from the group consisting of C$_1$–C$_6$ alkyl and phenyl, and r signifies 1 to 9; and (c) a compound selected from the group consisting of a compound of formula IIIa and a compound of formula III b

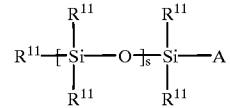

-continued

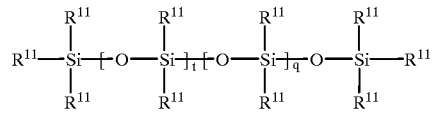

wherein

A signifies a bond to Sp, $R^{11}$ is selected from the group consisting of $C_1$–$C_6$ alkyl and phenyl, s signifies 4 to 250, t signifies 5 to 250, and q signifies 1 to 30;

with the proviso that at least one of $W^1$, $W^2$ and $W^3$ signifies SpSil, which process comprises:

a) reacting hydrosilane with an oligohydrosiloxane or a polyhydrosiloxane compound of the formula Sil—H, wherein Sil is as defined in formula I, with a compound Sp"XH, wherein X is O or NH, and Sp" has the same meaning as Sp as defined in formula I except that it has one degree of unsaturation more than Sp, at a temperature in the range of 0° to 200° C. in the presence of a metal catalyst to provide Sil—Sp—XH;

b) reacting Sil—Sp—XH with 4-aminobenzoic acid $C_{1-6}$ alkyl ester at a temperature in the range from 50° to 250° C. in the presence of a basic-, acidic-, or a Lewis acid catalyst to provide a compound of the formula C;

c-1) treating cyanuric acid chloride with a compound of the formula C

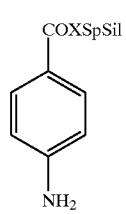

C

COXSpSil

NH₂ wherein Sp and Sil are as defined in formula I and X is O or NH above, at a temperature in the range from 20° to 280° C.; or c-2) treating cyanuric acid chloride either a first with 4-aminobenzoic acid $C_1$–$C_{20}$ alkyl ester at a temperature in the range from 0° to 40° C., and then with a compound of the formula C at a temperature in the range from 20° to 280° C., or treating cyanuric acid chloride at first with a compound of the formula C at a temperature in the range from 0° to 40° C. and then with 4-aminobenzoic $C_1$–$C_{20}$ alkyl ester at a temperature in the range from 20° to 280° C.

23. The process according to claim 22, wherein the temperature in step a) is from 40° to 110° C.

24. The process according to claim 22, wherein the temperature in step c-1) is from 50° to 150° C.

25. The process according to claim 22, wherein the treating in step c-1) is with a solvent.

26. The process according to claim 22, wherein the treating in step c-1) is free from the presence of a solvent.

27. A compound of the formula

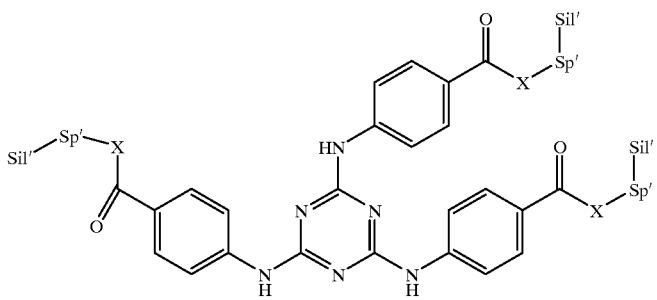

wherein

X is selected from the group consisting of O and NH;

Sp' is selected from the group consisting of a $C_3$–$C_{12}$ straight chain saturated hydrocarbon, a $C_3$–$C_{12}$ straight chain unsaturated hydrocarbon, a $C_3$–$C_{12}$ branched saturated hydrocarbon, and a $C_3$–$C_{12}$ branched unsaturated hydrocarbon;

Sil' is selected from the group consisting of (a) $SiR^1R^2R^3$, wherein $R^1$, $R^2$, and $R^3$ each independently signify $C_1$–$C_6$ alkyl, $C_1$–$C_6$ alkoxy, or phenyl; (b) $SiMe_m(OSiMe_3)_n$, wherein Me is methyl, m=0, 1, or 2, n=3, 2, or 1, and m+n=3, or a compound of the formula A, A', or B

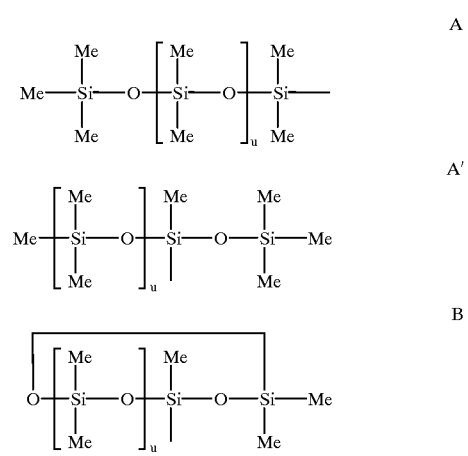

wherein Me is methyl and u is 0 to 6.

* * * * *